(12) United States Patent
Stock

(10) Patent No.: US 9,488,603 B2
(45) Date of Patent: Nov. 8, 2016

(54) METHOD, SYSTEM AND APPARATUS FOR NON-DESTRUCTIVE TESTING (NDT) OF POWER LINE SLEEVES, DEAD-ENDS AND OTHER COUPLINGS

(71) Applicant: Valard Construction Ltd., Edmonton (CA)

(72) Inventor: Calvin Stock, Lacombe (CA)

( * ) Notice: Subject to any disclaimer, the term of this patent is extended or adjusted under 35 U.S.C. 154(b) by 318 days.

(21) Appl. No.: 14/075,800

(22) Filed: Nov. 8, 2013

(65) Prior Publication Data

US 2014/0126695 A1 May 8, 2014

Related U.S. Application Data

(60) Provisional application No. 61/724,288, filed on Nov. 8, 2012.

(30) Foreign Application Priority Data

Nov. 8, 2012 (CA) ...................................... 2794497

(51) Int. Cl.
*G01N 23/04* (2006.01)
*G01N 23/18* (2006.01)
*G01R 31/02* (2006.01)

(52) U.S. Cl.
CPC .............. *G01N 23/04* (2013.01); *G01N 23/18* (2013.01); *G01N 2223/301* (2013.01); *G01N 2223/308* (2013.01); *G01N 2223/646* (2013.01); *G01R 31/022* (2013.01)

(58) Field of Classification Search
None
See application file for complete search history.

(56) References Cited

U.S. PATENT DOCUMENTS

| | | | | | |
|---|---|---|---|---|---|
| 3,521,059 | A * | 7/1970 | Stolle | ...................... | G01N 23/04 250/358.1 |
| 4,490,833 | A * | 12/1984 | Inomata | .................. | G01N 23/18 378/197 |
| 4,550,255 | A * | 10/1985 | Sve | ......................... | G01N 23/18 250/359.1 |
| 5,420,427 | A * | 5/1995 | Morgan | .................. | G01N 23/18 250/358.1 |
| 5,614,720 | A * | 3/1997 | Morgan | .................. | G01N 23/18 250/358.1 |
| 6,144,032 | A * | 11/2000 | Gazdzinski | .......... | G01N 23/222 250/269.6 |
| 6,300,634 | B1 * | 10/2001 | Gazdzinski | .......... | G01N 23/222 250/269.6 |
| 6,600,806 | B1 * | 7/2003 | Istar | ........................ | G01B 15/02 378/58 |
| 6,721,393 | B1 * | 4/2004 | Brauss | .............. | G01N 23/20016 378/196 |
| 6,853,706 | B2 * | 2/2005 | Brauss | .............. | G01N 23/20016 378/196 |
| 7,242,744 | B2 * | 7/2007 | Brauss | .............. | G01N 23/20016 378/189 |
| 7,800,061 | B2 * | 9/2010 | James | ...................... | G01N 23/06 250/308 |
| 8,280,145 | B2 * | 10/2012 | Kovarik | ................ | B66F 11/042 382/141 |
| 2008/0290302 | A1 * | 11/2008 | James | ...................... | G01N 23/06 250/522.1 |
| 2012/0033788 | A1 * | 2/2012 | Kovarik | ................ | B66F 11/042 378/58 |
| 2014/0126695 | A1 * | 5/2014 | Stock | ...................... | G01N 23/04 378/58 |

* cited by examiner

*Primary Examiner* — Thomas R Artman
(74) *Attorney, Agent, or Firm* — Antony C Edwards

(57) ABSTRACT

In one aspect the invention provides a system for non-destructive testing of overhead electrical power-line equipment. The system comprises a digital x-ray system and a support unit adapted to be suspended from said overhead electrical power-line equipment. The digital x-ray system comprises an x-ray source, an x-ray digital imager, an imager control unit and a wireless communication unit. The digital x-ray system is mounted on the support unit. Apparatus aspects for the support unit and method aspects are also provided.

26 Claims, 7 Drawing Sheets

METHOD, SYSTEM AND APPARATUS FOR NON-DESTRUCTIVE TESTING (NDT) OF POWER LINE SLEEVES, DEAD-ENDS AND OTHER COUPLINGS

CROSS REFERENCE TO RELATED APPLICATION

This application is a regular application of U.S. Provisional Patent Application Ser. No. 61/724,288 filed Nov. 8, 2012 and entitled, "METHOD, SYSTEM AND APPARATUS FOR NON-DESTRUCTIVE TESTING (NDT) OF POWER LINE SLEEVES, DEAD-ENDS AND OTHER COUPLING", the entirety of which is incorporated herein by reference.

FIELD OF THE INVENTION

The present invention relates generally to a method, system and apparatus for non-destructive testing (NDT) of overhead electrical powerline equipment. More particularly, the present invention relates to a method, system and apparatus for non-destructive testing (NDT) of overhead power line sleeves, dead-ends and other couplings.

BACKGROUND OF THE INVENTION

The background information discussed below is presented to better illustrate the novelty and usefulness of the present invention. This background information is not admitted prior art.

All electric utilities and their customers depend on system reliability. In the past, a common means of maintaining system reliability and reducing power outages was through preventative maintenance, which often requires the replacement of specific components after a certain life span, whether the components needed replacement or not. Many utilities have discovered that a better way to maintain system reliability is to practice predictive maintenance, where the emphasis is on finding the failing components, before they cause problems. Additionally, during construction of overhead power lines, it is desirable for electric utilities to have some inspection means of ensuring that the various components used during said construction are assembled correctly. Some of these components that would be desirable to test (whether during construction or as part of a predictive maintenance scheme) are power-line couplings, which include: (i) compression sleeves which join two ends of a power-line cable together and (ii) dead-ends which are utilized on power-line towers where the line changes direction (e.g. from running West to running North).

Industrial radiography is a known method for Non Destructive Testing, or NDT; that is, the material qualities of an object can be examined, tested and studied without destroying the object. For example, photographing the object with the help of gamma radiation makes it possible to discover different material defects such as poor welding seams or cracks. A typical situation in NDT radiography is where a gamma radiation source is being used to inspect a welded seam on a pipe or pipeline.

In gamma radiography, the radiation comes from a radioactive source, such as Iridium-192, for example. The radioactive source is typically placed in a portable protective container during storage and transport. In one design of equipment the source is stored in a block of lead or depleted uranium shielding that has an S-shaped tube-like hole through the block. In the safe position the source is in the center of the block and is attached to a metal wire that extends in both directions, to use the source a guide tube is attached to one side of the device while a drive cable is attached to the other end of the short cable. Using a hand-operated winch the source is then pushed out of the shield (to a radiating position) and along the source guide tube to the tip of the tube to expose the film. The film is usually placed in an appropriate position on the item being testes, e.g. on the section of pipe. Once the film has been sufficiently exposed to the radiation, the source is then cranked back into its fully shielded position.

Due to the radiation, industrial radiography usually has to be carried out outdoors or within shielded enclosures. The surrounding area must then be cordoned off and the radiation dose rate outside the barred area should not exceed certain levels (usually strictly regulated). Since a radioactive source can never be turned off; upon the completion of NDT exposure, the source must be redrawn into its shielded container. The operator must then check with a hand monitor that the source is safely back in its shielded position.

However, trying to adapt the techniques and equipment of industrial radiograph (that works well on pipelines) to overhead electrical power lines and their couplings such as compression sleeves and dead-ends, is problematic. Typically, such overhead lines are 80 feet above the ground, requiring the use of a man-basket lifted by a boom-truck or a crane to provide physical access thereto. This overhead work environment creates safety issues that are not normally found when working on ground level. For example, the radiation source could become stuck or suspended in the radiating position (such as due to a failure of the winch or the drive cable). In a ground level scenario, some lead shielding would simply be placed over the radiation source, while the problem was fixed. However, being suspended on an electrical power-line at a great height above the ground, trying to fully cover an exposed radiation source with lead shielding is highly problematic, if not impossible.

Moreover, the film used in gamma radiography also requires post-exposure chemical processing and developing. This takes time and limits the amount of NDT a person or work crew can do (on power-line compression sleeves and dead-ends) during a work day. The use of film is also problematic in terms of obtaining the appropriate "shots" or photos of the relevant area of the power-line coupling, since it takes time to develop the film and a re-take would slow down overall NDT production significantly.

Furthermore, due to the amount of shielding (often lead) in the protective container and length of drive cable (needed to work with gamma radiography from a safe distance), the typical weight of the equipment is often at least 80 lbs or more. Thus gamma radiography equipment is bulky, heavy and awkward, making it cumbersome and unwieldy to use in an overhead power-line environment.

Therefore, what is needed is a more efficient and safer method, system and apparatus for non-destructive testing (NDT) of overhead electrical power-line cables, sleeves, dead-ends and other couplings.

SUMMARY OF THE INVENTION

In one aspect the invention provides a system for non-destructive testing of overhead electrical power-line equipment. The system comprises a digital x-ray system and a support unit adapted to be suspended from said overhead electrical power-line equipment. The digital x-ray system comprises an x-ray source, an x-ray digital imager, an imager control unit and a wireless communication unit. The digital x-ray system is mounted on the support unit.

In another aspect the invention provides a support unit adapted to support a digital x-ray system having an x-ray digital imager and further adapted to be suspended from an overhead electrical power-line equipment. The support unit comprises a base having a longitudinal axis, a plurality of power-line attachment members projecting generally upward from the base, said plurality of power-line attachment members suitable to suspend the base below the overhead electrical power-line equipment and a plurality of imager support members suitable to mount the x-ray digital imager above the base and adjacent the overhead electrical power-line equipment. Method aspects are also provided.

BRIEF DESCRIPTION OF THE DRAWINGS

Embodiments of the invention will now be described, by way of example only, with reference to the accompanying drawings, wherein.

DETAILED DESCRIPTION OF THE PREFERRED EMBODIMENTS

Figure 1:
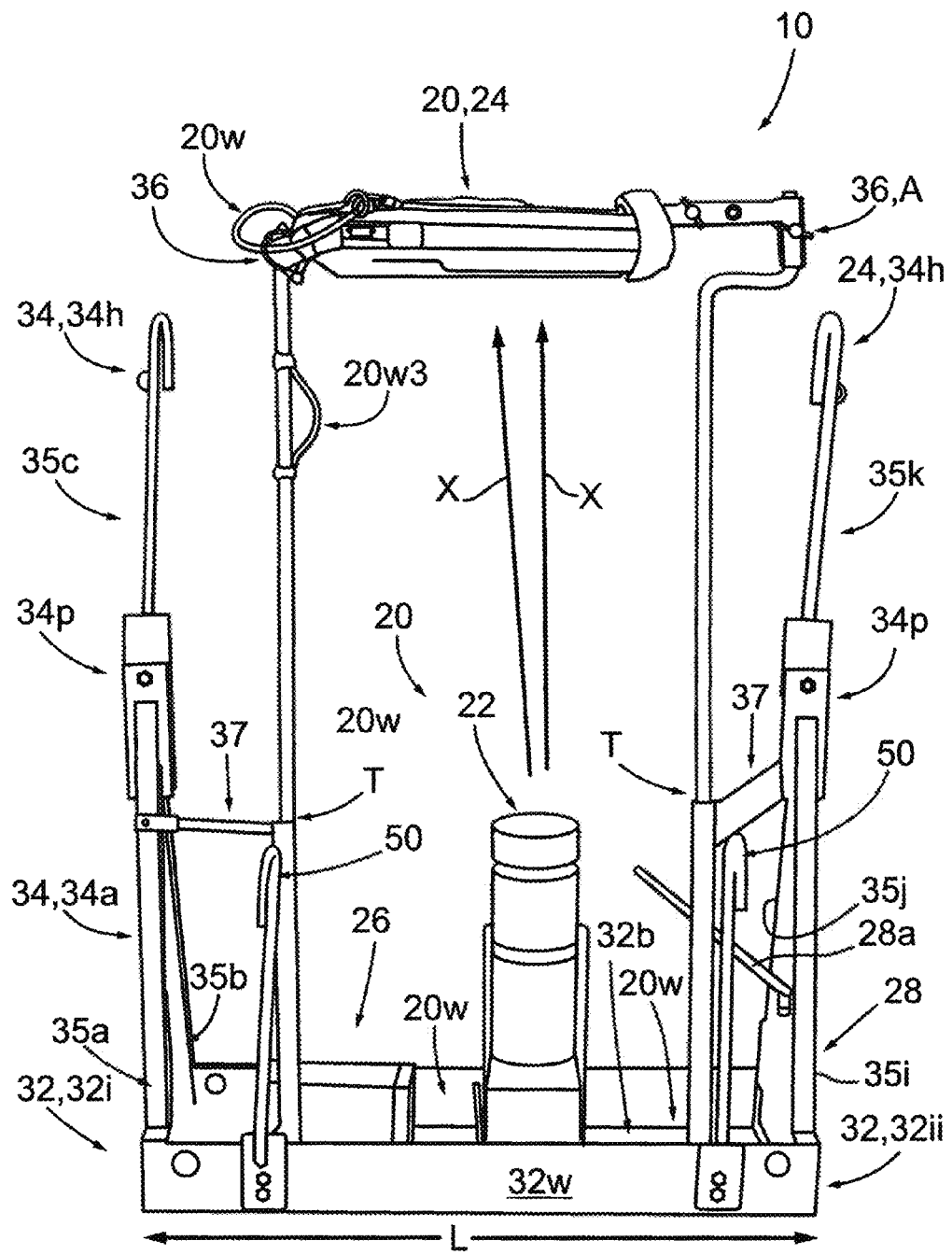
FIGS. 1 and 1A are perspective views of two embodiments of the invention, showing an x-ray source, imager control unit, flat panel imager and wireless communication unit all mounted in a support unit.

The following description is of a preferred embodiment by way of example only and without limitation to the combination of features necessary for carrying the invention into effect. Reference is to be had to the Figures in which identical reference numbers identify similar components. The drawing figures are not necessarily to scale and certain features may be shown in schematic or diagrammatic form in the interest of clarity and conciseness.

Referring now in detail to the accompanying drawings, there is illustrated an exemplary embodiment of apparatus, method and system according to the present invention, the system generally referred to by the numeral 10.

Figure 5:
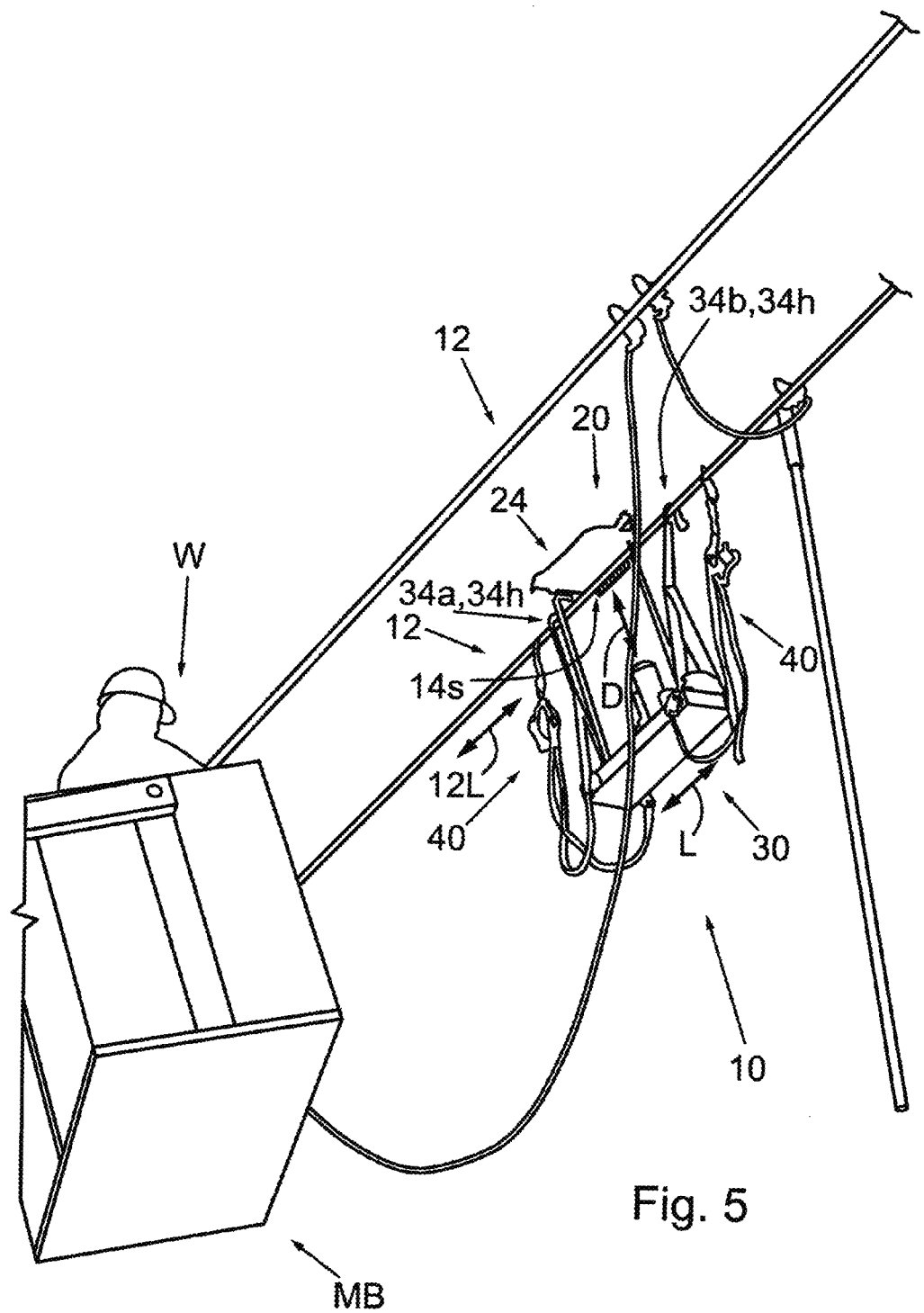
FIG. 5 is a perspective view of the embodiment of FIG. 1a, shown suspended from a power-line.

Referring now to FIGS. 1-5, a system 10 for non-destructive testing (NDT) of overhead electrical power-line equipment, such as power-line cabling 12 and power-line couplers 14, comprises a portable digital x-ray system 20 mounted in a support unit 30 adapted to be hung or suspended from said overhead electrical power-line cabling 12 (see FIG. 5). The term power-line coupler 14 as used herein includes power-line sleeves 14s and power-line dead-ends 14d as well as any other coupler that may be used in overhead electric power-lines.

The portable digital x-ray system 20 preferably comprises an x-ray source 22, a flat panel x-ray digital imager 24, an imager control unit (ICU) 26 and a wireless communication unit 28. Suitable portable digital x-ray system components, such as x-ray sources, flat panel digital imagers and imager control units (ICU) are manufactured and sold by Vidisco Ltd. of Or-Yehuda, Israel, including under the trademarks FLAT FOX-17™ and FOX-RAYZOR™. Wireless communication units are also manufactured and sold by Vidisco Ltd.

Figure 6A:
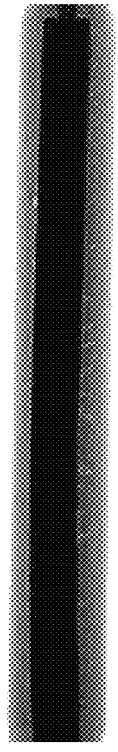
FIGS. 6a-6c are images produced of power-line couplers using the embodiment of FIG. 1, the images are shown inverted for easier visibility.
Figure 6B:
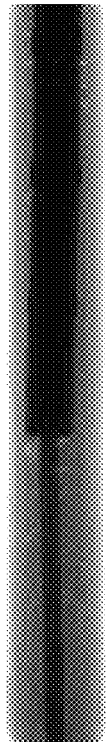
Figure 6C:
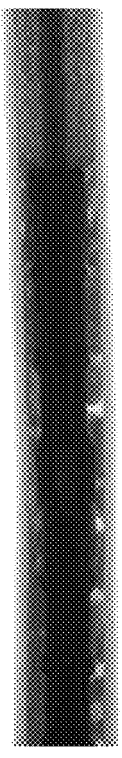

The inventor has found that, like an Iridium-192 gamma radiation source that is used in conventional gamma radiography of pipes, an x-ray source 22 provides suitable penetration of, and image resolution for, power-line cabling 12 and power-line couplers 14, so as to produce images appropriate for non-destructive testing (NDT) of said cabling 12 and couplers 14 for inspection and predictive maintenance purposes. A sampling of such images created by the system 10 of the embodiment of FIGS. 1-5 are shown in FIGS. 6a-6c.

In a preferred system 10 of the embodiment of FIGS. 1-5, the x-ray source 22 provides x-rays (illustrated diagrammatically by arrows labeled X) which may penetrate the cabling 12 and/or couplers 14. The x-rays X are provided on demand (i.e. when power is applied to the source 22 and it is actuated) and they are generally directed towards the flat panel digital imager 24 which is preferably positioned substantially on an opposing side of said cabling 12 and/or coupler 14 (as compared to the x-ray source 22); see FIGS. 1, 4 and 5. The imager 24 captures the x-rays X that may pass through the cabling 12 and/or couplers 14 at varying degrees and creates a digital image thereof which is representative of the state of the cabling 12 and/or couplers 14 and any defects that may exist therein (see FIGS. 6a-6c, for example of such images).

The imager control unit (ICU) 26 coordinates and serves as a control and communication interface between the x-ray source 22, the imager 24, the wireless communication unit 28 and a remote computer (such as a laptop, not shown) to initiate, capture and transmit digital x-ray images taken by the system 10 (to said remote computer, not shown). The imager control unit (ICU) 26 also provides power to the system 10 and may have a suitable large-capacity battery so as to provide portability and power to the system 10 and allow for prolonged operation of the system 10 on a section of power-line cabling 12 without having to re-charge. Preferably, appropriate wiring and connectors 20w are provided to operationally connect the imager control unit (ICU) 26 to the x-ray source 22, the imager 24 and the wireless communication unit 28.

The wireless communication unit 28 provides for wireless communication between the system 10 and a remote computer (not shown), preferably via a WiFi communication protocol or the like, so as to transmit digital x-ray NDT images taken by the system 10 to said remote computer. The wireless communication unit 28 may be part of the ICU 26 or a separate component (as shown in the preferred embodiment in FIGS. 1-5). Preferably, the wireless communication unit 28 has an antenna 28a to permit radio or WiFi transmission of the NDT images (take by the system 10) down to a remote computer or laptop some distance away (such as on the ground or in a ground-based mobile station); and also to transmit control signals from the remote computer back up to the system 10, such as signals to have the system 10 take a digital x-ray image of a coupler 14.

The support unit 30 is adapted to be suspended from an overhead electrical power-line cable 12 and preferably comprises a base 32 to support and mount the majority of the components of the portable digital x-ray system 20 (such as the x-ray source 22, imager control unit (ICU) 26 and wireless communication unit 28), one or more power-line attachment members 34, projecting generally upward from the base 32, to suspend the base 32 from the power-line cable 12, and one or more imager support members 36 to support and mount the imager 24 at a suitable location adjacent (or above) the cable 12 or coupler 14 that is to be imaged. Preferably, the one or more power-line attachment members 34 terminate in a hook 34h suitable to hook or loop around the power-line cable 12, or coupler 14, and thereby suspend the support unit 30 from said cable 12 or coupler 14 (as more clearly shown in FIGS. 1, 4 and 5). More preferably the one or more imager support members 36 telescope, such as at position T (or otherwise adjust, such as at position A), so as to allow for fine spatial adjustment of the imager 24 relative to the cable 12 or coupler 14 that is to be imaged.

Advantageously, by utilizing hooks 34h to suspend the support unit 30 from the cable 12 or coupler 14, a set of NDT images of same can be taken by simply sliding or moving the support unit 30 along the cable 12 or coupler 14 and then taking each image, the set of images then comprising a full NDT inspection of said cable 12 section or coupler 14.

The base 32 is preferably in the form of a rectangular tray or basket (having a bottom 32b and side walls 32w, as shown in the Figures) wherein, when the support unit 30 is suspended from an overhead electrical power-line cable 12, its longitudinal axis (illustrated by an arrow labeled L) is substantially parallel to the longitudinal axis of the cable 12 (illustrated by an arrow labeled 12L), see FIG. 5. Advantageously, such a rectangular configuration of the base 32, and such parallel alignment of its longitudinal axis L along the length of cable 12L, aids in the stability of the support unit 30 while suspended from the cable 12 and minimizes swinging and movement of the system 10 during operation. More advantageously, having side walls 32w, various components of the digital x-ray system 20, including the wiring and connectors 20w, are more securely contained within the support unit 30.

Preferably, the majority of the components of portable digital x-ray system 20, such as the x-ray source 22, imager control unit (ICU) 26 and wireless communication unit 28, are mounted to the base 32 and are arranged in a serial manner (i.e. one next to the other) in substantially the center of the base 32 and along its longitudinal axis L, see FIG. 1. Advantageously, by mounting the majority of the components of portable digital x-ray system 20 (such as the x-ray source 22, imager control unit (ICU) 26 and wireless communication unit 28) in the base 32 and suspending said base 32 below the cable 12 or coupler 14 to be imaged (as opposed to positioning said components above or beside such cable or coupler), additional stability is provided to the system 10 during NDT operations. More advantageously, the serial arrangement of the majority of the digital x-ray system 20 components along substantially the centerline of the base 32 further aids in the stability of the support unit 30 while it is suspended from the cable 12 and further minimizes any swinging and shaking movement of the system 10 that may otherwise occur during NDT operations.

In the preferred embodiment of FIGS. 1-5, there are two power-line attachment members 34a, 34b connected substantially at either longitudinal end 32i, 32ii of the rectangular base, as more clearly shown in the Figures. Moreover, in the preferred embodiment of FIGS. 1-5, the attachment members 34a, 34b are each shaped as an inverted Y, each Y-shape having a set of paired arms (items 35a, 35b and 35i, 35j respectively) and a central trunk (items 35c and 35k respectively), wherein the arms (items 35a, 35b and 35i, 35j respectively) attach to the base and the central trunk (items 35c and 35k respectively) projects upward and away from the base 32, the distal ends thereof forming a hook 34h. The inventor has found that this inverted Y-shape and arrangement of the two power-line attachment members 34a, 34b at either longitudinal end of the base 32 enhances the stability of the support unit 30 while it is suspended from the cable 12. The inventor has also found that having two imager support members 36 positioned on the base 32 a few inches inward (i.e. medially) from the power-line attachment members 34 (which are position at either end of the base 32) and then preferably providing a connecting member 37 between each pair of members 34 and 36 (see FIG. 1) further enhances the stability of the support unit 30 while it is suspended from the cable 12.

Figure 1A:
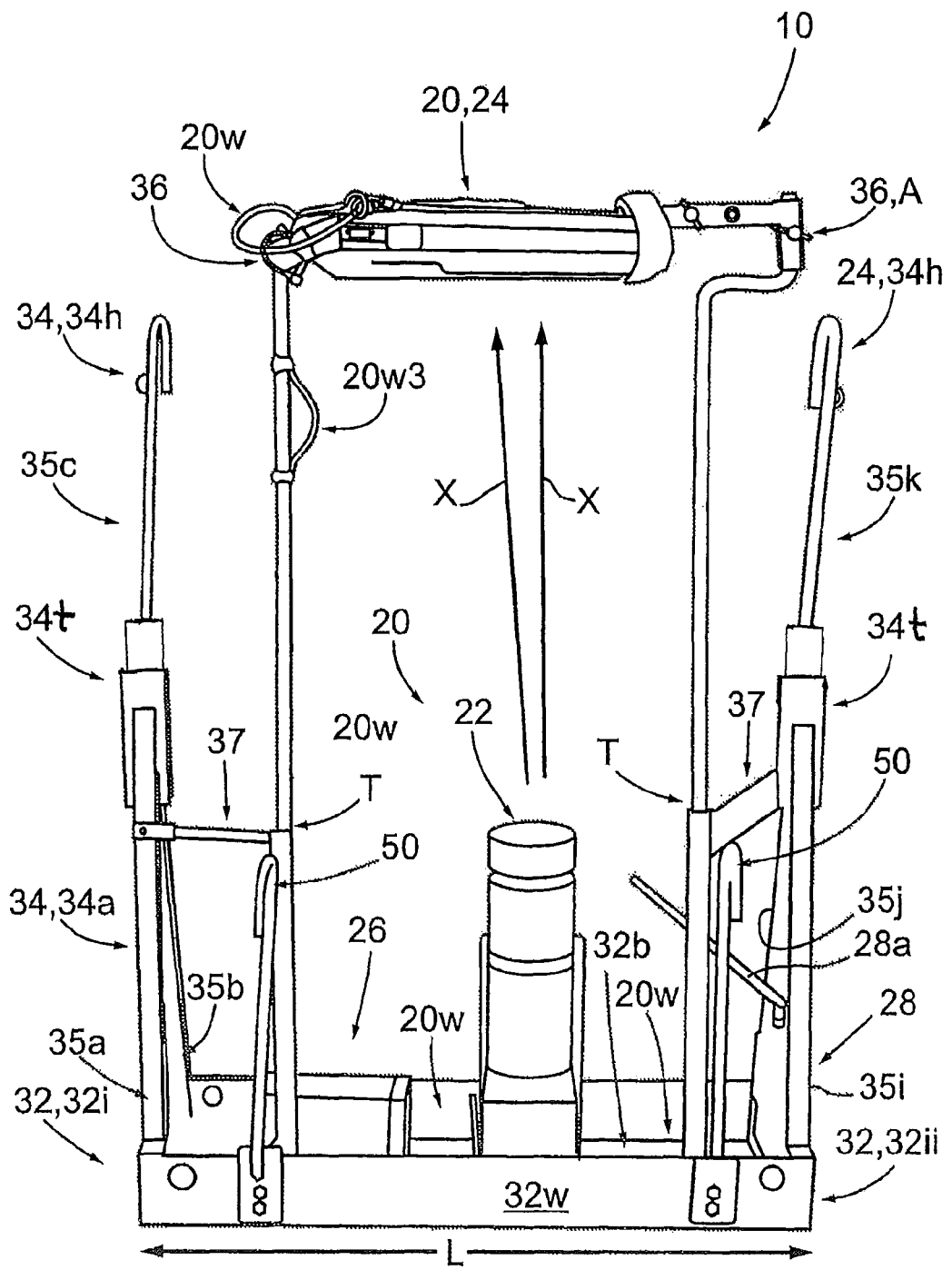

Preferably, the one or more power-line attachment members 34a, 34b are each provided with a pivot 34p to allow side-to-side adjustment of said members 34a, 34b (compare orientation of the central trunks 35c, 35k in FIG. 1 with that in FIG. 3) and thereby allow the support unit 30 to attach to cabling 12 or couplers 14 that may be oriented at an angle or somehow otherwise offset from the normal straight-line run of said cabling 12. The pivot 34p may be at substantially the center point of the inverted Y members 34a, 34b (see FIG. 2b, for example). More preferably, in another embodiment (see FIG. 1A), the one or more power-line attachment members 34a, 34b are each provided with telescoping means 34t, 34t in a conventional manner, to allow adjustment to distance between the base 32 and cable 12 (from which the unit 30 is suspended or hung during NDT operations), so as to adjust focal distance D from the x-ray source 22 to the cable 12 or coupler 14 that is being imaged by the imager 24.

Figure 2A:
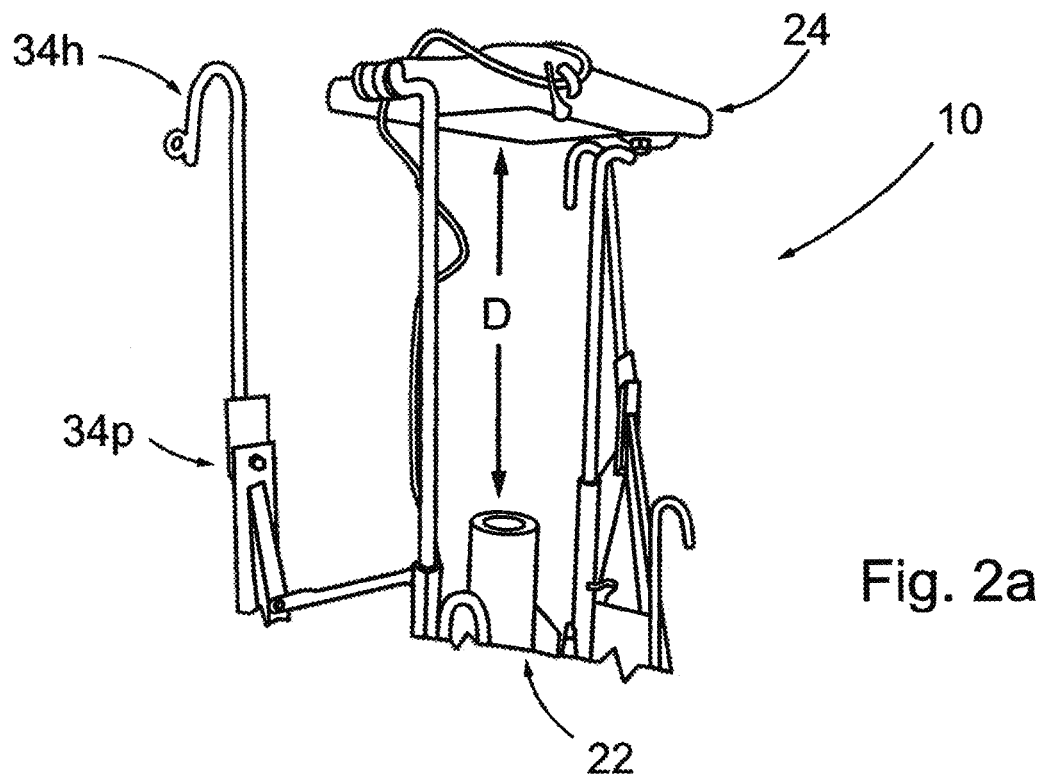
FIGS. 2a and 2b are side perspective views of the top and bottom halves, respectively, of the embodiment of FIG. 1.
Figure 2B:
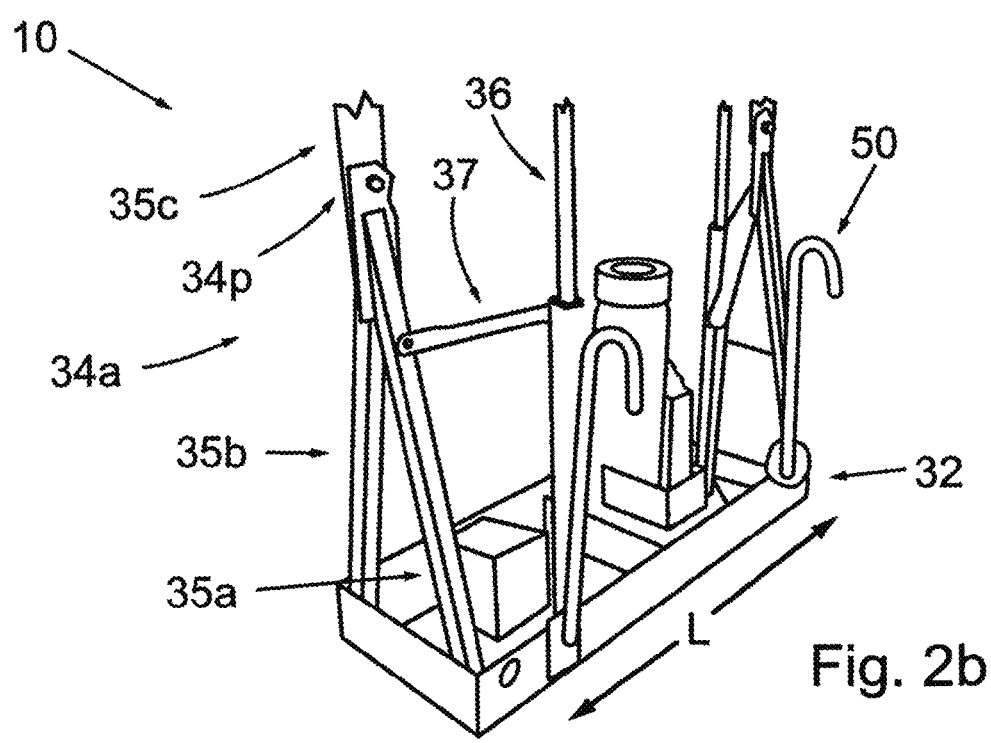
Figure 3:
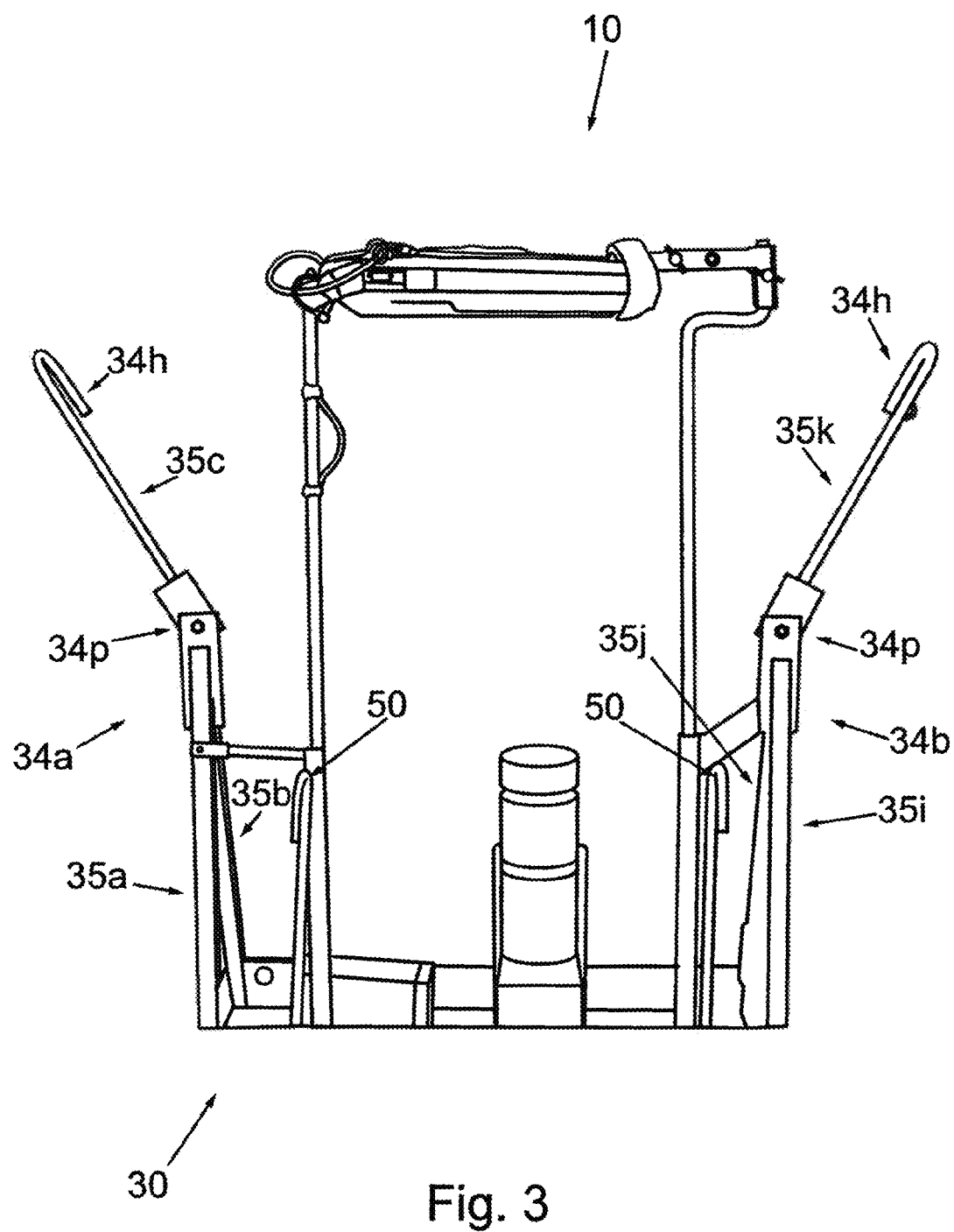
FIG. 3 is a perspective view of the embodiment of FIG. 1, showing the power-line attachment members in an adjusted position.
Figure 4:
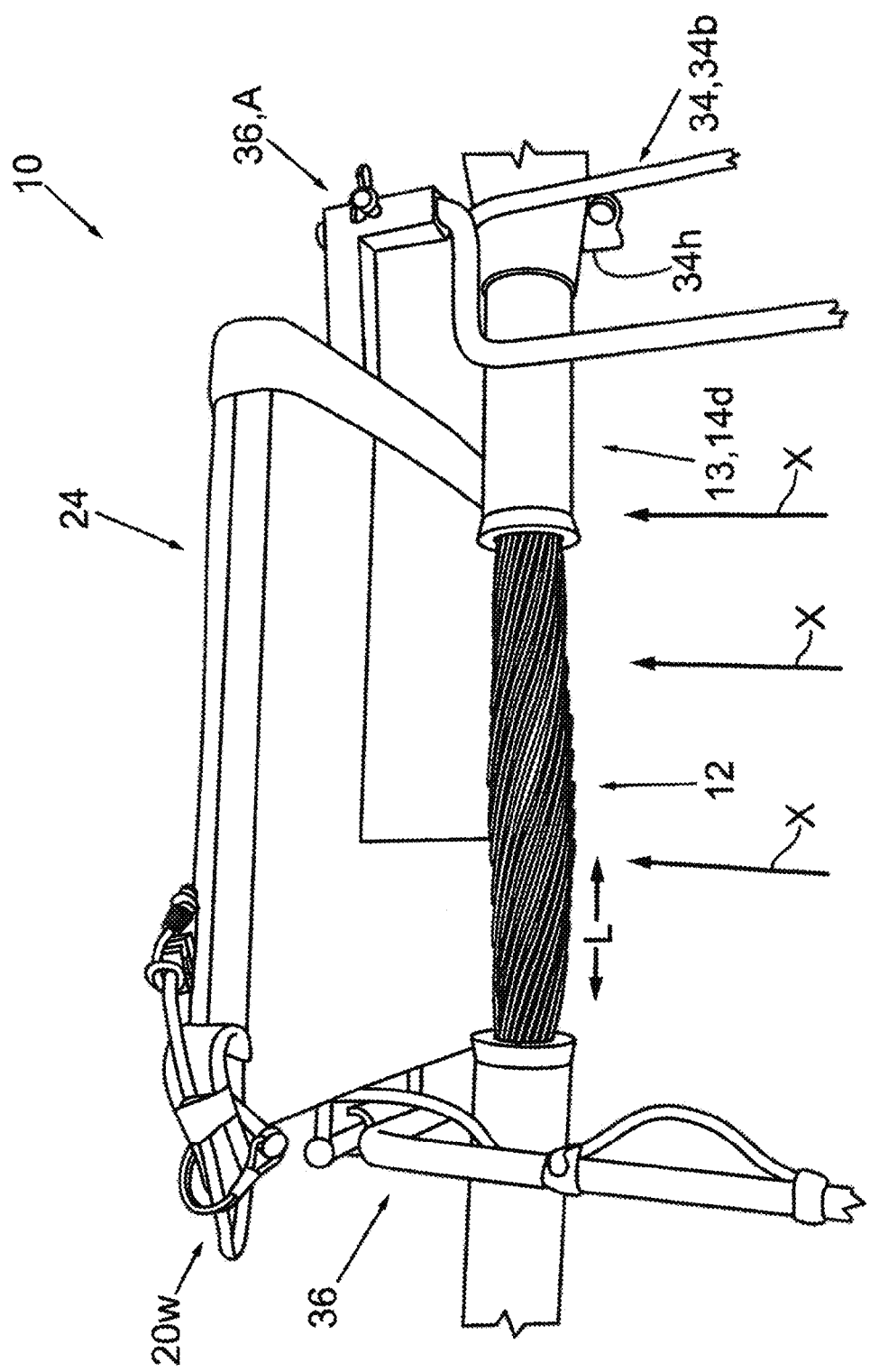
FIG. 4 is a perspective view of the top portion of the embodiment of FIG. 1a, showing a power-line coupler positioned adjacent the flat panel imager.

The inventor has found that a suitable focal distance D (to allow for clear and sharp NDT images to be taken) between the focal point of the x-ray source 22 and imager 24 is approximately 45 to 55 cm, with 50 cm being most preferable (see FIGS. 2a and 5). Moreover, the inventor has found that by having the imager 24 closely positioned adjacent to the cable 12 or coupler 14 to be imaged (or even touching same), with perhaps only a few centimeters of space between said cable 12 or coupler 14 and the imager 24, clear and sharp NDT images of same can be taken. That is, the support unit 30 provides adjustments and allows for the positioning and arrangement of the imager 24 close to and adjacent the item to be imaged (e.g. a coupler 14) while still providing sufficient focal distance between said imager 24 and the x-ray source 22 to allow for suitable NDT imaging of said item to be imaged.

Preferably attachment members 34a (or central trunks thereof, i.e. items 35c and 35k, if said members are provided as an inverted Y) and imager support members 36 are arranged in a serial manner (i.e. one next to the other) in substantially the center of the base 32 and along the base's longitudinal axis L. The inventor has found that such arrangement of members 34 and 36 aids in the stability of the support unit 30 while it is suspended from the cable 12 and further minimizes any swinging and shaking movement of the system 10 that may otherwise occur during NDT operations Preferably, the base 32, the one or more power-line attachment members 34 and the one or more imager support members 36 are all constructed of aluminum, so as to reduce the weight of the support unit 30 (as compared to being constructed of other metals, such as steel, lead or depleted uranium) while still retaining sufficient strength to mount the digital x-ray system 20.

Advantageously, the digital x-ray NDT radiography system 10 of the present invention provides digital images in near "real-time", thereby increasing the speed at which power-line cabling 12 and couplers 14 can be examined or tested as compared to traditional film-based gamma radiography (which require chemical processing). More advantageously, the digital x-ray NDT radiography of the preferred system 10 allows for quick and easy "re-takes" of images, should that be necessary. Even more advantageously, by using an x-ray source 22, the various disadvantages associated with gamma radiography, including the safety concerns, are eliminated—because the x-ray source 22 ceases to emit x-ray radiation once the power has been shut off, and hence does not need any kind of protective shielding. Yet even more advantageously, the digital x-ray NDT radiography of the preferred system 10 weighs significantly less (at approximately 30 to 35 lbs) when constructed of aluminum, as compared to a conventional portable gamma radiography system (which typically weighs approximately 80 lbs), thereby placing less stress on any overhead power-lines 12 that the system 10 may be suspended or hung from (as compared to a conventional gamma radiography system).

Preferably, safety straps 40 are provided as a secondary, or back-up, connection of the system 10 to an overhead power-line cable 12 (see FIG. 5). Advantageously, such safety straps 40 will provide security and peace of mind (that the system will not fall 80 feet to the ground) to an NDT operator or worker W when lifting and/or sliding the support unit 30 along a coupler 14 to take images of adjacent sections.

Preferably, one or more man-basket hooks 50 are provided to the support unit 30, which are suitable to hook or connect the system 10 to the outside of a man-basket MB and thereby: (i) assist in lifting the system 10 up to the height of the overhead power-line (as said man-basket is lifted) and (ii) not have the system 10 take up valuable room inside the man-basket MB that would otherwise be taken-up if the system 10 was lifted and carried therewithin. More preferably, there are two man-basket hooks 50 mounted to one (longitudinal) side of the base 32 and positioned substantially near each end 32i, 32ii as shown in FIGS. 1-5.

Operation

As will be gathered from the description above, safe and efficient NDT imaging operations of overhead power-line cabling 12 and couplers 14 can be conducted using a preferred method as follows:

providing a system 10 having a support unit 30 housing a digital portable x-ray system 20 having an x-ray source 22 and a digital flat panel imager 24;

lifting the support unit 30 to said cabling 12 and/or couplers 14, preferably using man-basket hooks 50 connected to a man-basket MB;

suspending the support unit 30 from said cabling 12 and/or couplers 14, preferably using power-line attachment members 34 having hooked ends 34h;

preferably also connecting the system 10 to the overhead power-line cabling 12 using one or more safety straps 40;

preferably mounting the majority of the components of portable digital x-ray system 20 (such as the x-ray source 22, an imager control unit (ICU) 26 and a wireless communication unit 28) in a base 32 and suspending said base 32 below the cable 12 and/or coupler 14 to be imaged;

positioning the digital flat panel imager 24 as close to the cabling 12 and/or couplers 14 that are being imaged, preferably adjusting said positioning using imager support members 36 and, more preferably, positioning said imager 24 substantially above said cabling 12 and/or couplers 14;

positioning an x-ray source 22 below said imager 24, with said cabling 12 and/or couplers 14 positioned between the source 22 and imager 24 and, preferably with a focal distance in the range of 45 to 55 cm;

taking one or more digital images of said cabling 12 and/or couplers 14 utilizing the x-ray system 20; and preferably transmitting said digital images to a remote computer using a wireless communication unit 28.

In the claims, the word "comprising" is used in its inclusive sense and does not exclude other elements being present. The indefinite article "a" before a claim feature does not exclude more than one of the features being present. Those of ordinary skill in the art will appreciate that various modifications to the invention as described herein will be possible without falling outside the scope of the invention.

What is claimed is:

1. A system for non-destructive testing of overhead electrical power-line equipment, the system comprising:
a digital x-ray system comprising an x-ray source, an x-ray digital imager, an imager control unit and a wireless communication unit, and
a support unit comprising a base and a plurality of attachment members, each attachment member of said plurality of attachment members having a lower end and an upper end, each lower end coupled to the base and each upper end adapted to be releasably coupled to the overhead electrical power-line equipment,
wherein at least one attachment member of the plurality of attachment members has an adjustable length,
wherein the digital x-ray system is mounted on the base,
whereby the plurality of attachment members suspend the base and at least a base portion of the digital x-ray system below the overhead electrical power-line equipment when the upper ends of the attachment members are mounted thereon.

2. The system of claim 1 wherein the base portion of the digital x-ray system includes the x-ray source, the imager control unit and the wireless communication unit.

3. The system of claim 1 wherein the upper ends of the plurality of attachment members each terminate in a hook, and wherein the hook is suitable to releasably couple the support unit to the overhead electrical power-line equipment.

4. The system of claim 1 wherein the support unit further comprises a plurality of imager support members for positioning the x-ray digital imager above and substantially adjacent to the overhead electrical power-line equipment when the attachment members are mounted thereon.

5. The system of claim 4 wherein the plurality of imager support members further comprise telescoping adjusters, so as to allow for substantially vertical adjustment of a distance between the x-ray digital imager and the overhead electrical power-line equipment.

6. The system of claim 1 wherein the support unit further comprises at least one man-basket hook.

7. The system claim 1 wherein the x-ray digital imager is mounted on at least one imager support member so as to be adjacent to and above the upper ends of the plurality of attachment members.

8. The system of claim 1 wherein the spatial adjuster of each of the plurality of attachment members are selected from a group comprising: angular adjusters, lengthening adjusters, so as to allow for adjustment of a distance between the base and the overhead electrical power-line equipment when the attachment members are mounted thereon.

9. The system of claim 8 wherein the lengthening adjusters comprise telescoping adjusters.

10. The system of claim 8 wherein the angular adjusters comprise pivoting adjusters.

11. The system of claim 1 wherein the base comprises a first longitudinal axis and the overhead electrical power-line equipment comprises a second longitudinal axis, wherein when the support unit is suspended from the overhead electrical power-line equipment the first longitudinal axis is substantially parallel to the second longitudinal axis.

12. The system of claim 11 wherein the base further comprises a first end and a second end substantially opposite the first end along the first longitudinal axis, wherein a first attachment member of said plurality of attachment members is coupled to substantially the first end and a second attachment member of said plurality of attachment members is coupled to substantially the second end.

13. The system of claim 12 wherein each of the first and second attachment members further comprise two lower legs and one upper leg wherein the two lower legs are each coupled to the base and the upper leg is proximate the overhead electrical power-line equipment when the attachment members are mounted thereon.

14. A support unit for supporting a digital x-ray system, which includes an x-ray source and an x-ray digital imager, from overhead electrical power-line equipment, the support unit comprising:
a base having a longitudinal axis,
a plurality of attachment members, each attachment member of said plurality of attachment members having a lower end and an upper end, each lower end coupled to the base and each upper end configured to be releasably coupled to the overhead electrical power-line equipment,
a plurality of support members for positioning the x-ray digital imager and x-ray source on opposite sides of the overhead electrical power-line equipment when the plurality of attachment members are mounted thereon and the x-ray system is mounted on the base and the plurality of support members, each support member of the plurality of support members having a lower end and an upper end, each lower end coupled to the base, wherein at least one attachment member of the plurality of attachment members has an adjustable length.

15. The support unit of claim 14 wherein the plurality of support members further comprise telescoping adjusters, so as to allow for substantially vertical adjustment of a distance between upper ends of the plurality of support members and the upper ends of the plurality of attachment members.

16. The support unit of claim 14 wherein the upper ends of the plurality of attachment members each terminate in a hook so as to releasably couple the support unit to the overhead electrical power-line equipment.

17. The support unit of claim 14 wherein the base further comprises a first end and a second end substantially opposite the first end along the longitudinal axis, wherein a first attachment member of said plurality of attachment members is coupled to substantially the first end and a second attachment member of said plurality of attachment members is coupled to substantially the second end.

18. The support unit of claim 17 wherein each of the first and second attachment members further comprise two lower legs and one upper leg wherein the two lower legs are each coupled to the base and the upper leg is proximate the overhead electrical power-line equipment.

19. The support unit of claim 18 further comprising at least one man-basket hook.

20. A method for non-destructive testing of overhead electrical power-line equipment using the support unit of claim 14, the method comprising the steps of:
providing the support unit of claim 14,
suspending the support unit from the overhead electrical power-line equipment using at least one of the plurality of attachment members,
positioning the x-ray digital imager proximate to and above the overhead electrical power-line equipment, using the spatial adjusters,
mounting and positioning the x-ray source on the base so as to position the x-ray source aligned below the x-ray digital imager so that the x-ray source and the x-ray digital imager are aligned on opposite sides of the overhead electrical power-line equipment.

21. The method of claim 20 further comprising:
taking and transmitting at least one digital image to a remote computer using a wireless communication unit.

22. The method of claim 20 further comprising:
actuating at least one of the spatial adjusters to set a focal distance between the x-ray source and the overhead electrical power-line equipment in a range of 45 to 55 cm.

23. The support unit of claim 14 wherein the support members are imager support members adapted to support the x-ray imager.

24. The support unit of claim 14 wherein the spatial adjuster of each of the plurality of attachment members are selected from a group comprising: angular adjusters, lengthening adjusters, so as to allow for substantially vertical adjustment of a distance between the base and the upper ends of the attachment members.

25. The system of claim 24, wherein the lengthening adjusters comprise telescoping adjusters.

26. The system of claim 24, wherein the angular adjusters comprise pivoting adjusters.

* * * * *